United States Patent
Rich et al.

(10) Patent No.: US 7,857,005 B2
(45) Date of Patent: *Dec. 28, 2010

(54) PULSATION ATTENUATOR FOR A FLUIDIC SYSTEM

(75) Inventors: Collin A. Rich, Ypsilanti, MI (US); Nathaniel C. Bair, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/425,830

(22) Filed: Apr. 17, 2009

(65) Prior Publication Data

US 2009/0260701 A1    Oct. 22, 2009

Related U.S. Application Data

(63) Continuation-in-part of application No. PCT/US2007/004836, filed on Feb. 22, 2007, and a continuation-in-part of application No. 11/958,278, filed on Dec. 17, 2007, now Pat. No. 7,520,300.

(60) Provisional application No. 61/014,382, filed on Dec. 17, 2007.

(51) Int. Cl.
*F16L 55/04* (2006.01)

(52) U.S. Cl. .............. 138/30; 138/31; 138/26; 137/207

(58) Field of Classification Search ........... 138/26, 138/30, 31, 40, 41, 42
See application file for complete search history.

(56) References Cited

U.S. PATENT DOCUMENTS

| | | | |
|---|---|---|---|
| 3,347,273 A * | 10/1967 | Russell | ......... 138/30 |
| 3,601,128 A * | 8/1971 | Hakim | ......... 604/9 |
| 3,672,402 A | 6/1972 | Bloemer | |
| 4,112,735 A | 9/1978 | McKnight | |
| 4,138,879 A | 2/1979 | Liebermann | |
| 4,371,786 A | 2/1983 | Kramer | |
| 4,448,538 A | 5/1984 | Mantel | |
| 4,559,454 A | 12/1985 | Kramer | |
| 4,790,653 A | 12/1988 | North, Jr. | |
| 4,818,103 A | 4/1989 | Thomas et al. | |
| 4,844,610 A | 7/1989 | North, Jr. | |
| 5,040,890 A | 8/1991 | North, Jr. | |
| 5,043,706 A | 8/1991 | Oliver | |
| 5,083,862 A | 1/1992 | Rusnak | |
| 5,155,543 A | 10/1992 | Hirako | |

(Continued)

FOREIGN PATENT DOCUMENTS

EP    1521076    9/2004

(Continued)

*Primary Examiner*—Patrick F Brinson
(74) *Attorney, Agent, or Firm*—Jeffrey Schox

(57) ABSTRACT

A pulsation attenuator for a fluidic system with a fluidic pump. The pulsation attenuator includes a fluidic channel, a first fluidic device adapted to attenuate pulsations, and a second fluidic device adapted to attenuate pulsations. Preferably, the first fluidic device includes a first fluidic resistor and a first fluidic capacitor, and the second fluidic device includes a second fluidic resistor and a second fluidic capacitor. Preferably, the first fluidic resistor and second fluidic resistor are resistive channels. Preferably, the first fluidic capacitor and second fluidic capacitor include a membrane that expands and accumulates fluid and then contracts and reintroduces the accumulated fluid into the fluidic channel.

22 Claims, 6 Drawing Sheets

U.S. PATENT DOCUMENTS

| | | | |
|---|---|---|---|
| 5,395,588 A | 3/1995 | North, Jr. et al. | |
| 5,403,552 A | 4/1995 | Pardikes | |
| 5,539,386 A | 7/1996 | Elliott | |
| 5,552,885 A | 9/1996 | Steen | |
| 5,797,430 A * | 8/1998 | Becke et al. | 138/30 |
| 6,039,078 A | 3/2000 | Tamari | |
| 6,070,477 A | 6/2000 | Mark | |
| 6,110,427 A | 8/2000 | Uffenheimer | |
| 6,156,208 A | 12/2000 | Desjardins et al. | |
| 6,183,697 B1 | 2/2001 | Tanaka et al. | |
| 6,288,783 B1 | 9/2001 | Auad | |
| 6,382,228 B1 | 5/2002 | Cabuz et al. | |
| 6,427,521 B2 | 8/2002 | Jakkula et al. | |
| 6,431,950 B1 | 8/2002 | Mayes | |
| 6,456,769 B1 | 9/2002 | Furusawa et al. | |
| 6,568,271 B2 | 5/2003 | Shah et al. | |
| 6,602,469 B1 | 8/2003 | Maus et al. | |
| 6,694,799 B2 | 2/2004 | Small | |
| 6,718,415 B1 | 4/2004 | Chu | |
| 6,825,926 B2 | 11/2004 | Turner et al. | |
| 6,852,284 B1 | 2/2005 | Holl et al. | |
| 6,872,180 B2 | 3/2005 | Reinhardt et al. | |
| 6,901,964 B2 * | 6/2005 | Kippe et al. | 138/30 |
| 6,908,226 B2 | 6/2005 | Siddiqui et al. | |
| 6,912,904 B2 | 7/2005 | Storm, Jr. et al. | |
| 6,941,005 B2 | 9/2005 | Lary et al. | |
| 7,019,834 B2 | 3/2006 | Sebok et al. | |
| 7,061,595 B2 | 6/2006 | Cabuz et al. | |
| 7,105,355 B2 | 9/2006 | Kurabayashi et al. | |
| 7,328,722 B2 | 2/2008 | Rich | |
| 7,403,125 B2 | 7/2008 | Rich | |
| 7,520,300 B2 | 4/2009 | Rich | |
| 7,628,956 B2 | 12/2009 | Jindo | |
| 2002/0028434 A1 | 3/2002 | Goix et al. | |
| 2002/0059959 A1 | 5/2002 | Qatu et al. | |
| 2002/0123154 A1 | 9/2002 | Burshteyn | |
| 2003/0054558 A1 | 3/2003 | Kurabayashi | |
| 2003/0062314 A1 | 4/2003 | Davidson et al. | |
| 2003/0072549 A1 | 4/2003 | Facer et al. | |
| 2003/0129090 A1 | 7/2003 | Farrell | |
| 2003/0175157 A1 | 9/2003 | Micklash, II et al. | |
| 2003/0202175 A1 | 10/2003 | Van den Engh et al. | |
| 2003/0211009 A1 | 11/2003 | Buchanan | |
| 2003/0223061 A1 | 12/2003 | Sebok | |
| 2004/0031521 A1 | 2/2004 | Vrane et al. | |
| 2004/0112808 A1 | 6/2004 | Takagi et al. | |
| 2004/0123645 A1 | 7/2004 | Storm, Jr. et al. | |
| 2005/0069454 A1 | 3/2005 | Bell | |
| 2005/0195684 A1 | 9/2005 | Mayer | |
| 2005/0252574 A1 | 11/2005 | Khan et al. | |
| 2006/0177937 A1 | 8/2006 | Kurabayashi et al. | |
| 2006/0286549 A1 | 12/2006 | Sohn et al. | |
| 2007/0003434 A1 | 1/2007 | Padmanabhan et al. | |
| 2007/0212262 A1 | 9/2007 | Rich | |
| 2007/0224684 A1 | 9/2007 | Olson et al. | |
| 2007/0243106 A1 | 10/2007 | Rich | |
| 2009/0104075 A1 | 4/2009 | Rich | |

FOREIGN PATENT DOCUMENTS

| | | |
|---|---|---|
| WO | 2005017499 | 8/2004 |

* cited by examiner

PULSATION ATTENUATOR FOR A FLUIDIC SYSTEM

CROSS-REFERENCE TO RELATED APPLICATIONS

This application is a continuation-in-part of prior application Ser. No. 11/958,278 filed 17 Dec. 2007, which is a continuation of prior application Ser. No. 11/297,667 filed 7 Dec. 2005 (issued as U.S. Pat. No. 7,328,722). Both prior patent applications are incorporated in their entirety by this reference.

TECHNICAL FIELD

This invention relates generally to the fluidic system field, and more specifically to a new and useful fluidic system in the flow cytometer field.

BACKGROUND

There are many cases, such as in flow cytometery, where a steady, pulse-free fluidic stream is desirable for a fluidic system. However, fluidic pumps, pressure variations, supply fluid variations, and/or many other aspects of a fluidic system introduce disturbances to the fluidic system. These disturbances result in fluctuations in the fluidic pressure and flow within the system. Thus, there is a need in the fluidic system field to create a new and useful pulsation attenuating fluidic system. This invention provides such new and useful system.

DESCRIPTION OF THE PREFERRED EMBODIMENTS

The following description of the preferred embodiment of the invention is not intended to limit the invention to this preferred embodiment, but rather to enable any person skilled in the art of fluidic systems for flow cytometers to make and use this invention.

1. The Pulsation Attenuator of the First Preferred Embodiment

Figure 1:
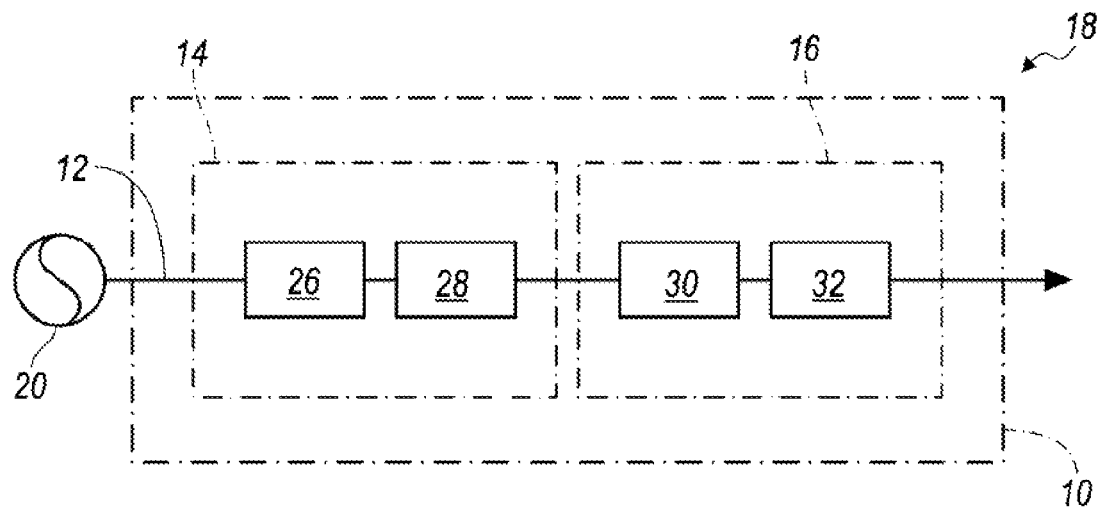
FIG. 1 is schematic representation of the pulsation attenuator of the first preferred embodiment in a fluidic system with a fluidic pump.

As shown in FIG. 1, the pulsation attenuator 10 of the preferred embodiments includes a fluidic channel 12, a first fluidic device 14 adapted to attenuate pulsations, and a second fluidic device 16 adapted to attenuate pulsations. The pulsation attenuator 10 has been specifically designed for a fluidic system 18 of a flow cytometer with a fluidic pump 20, such as a peristaltic pump, but may be alternatively used in any suitable fluidic system.

Figure 2:
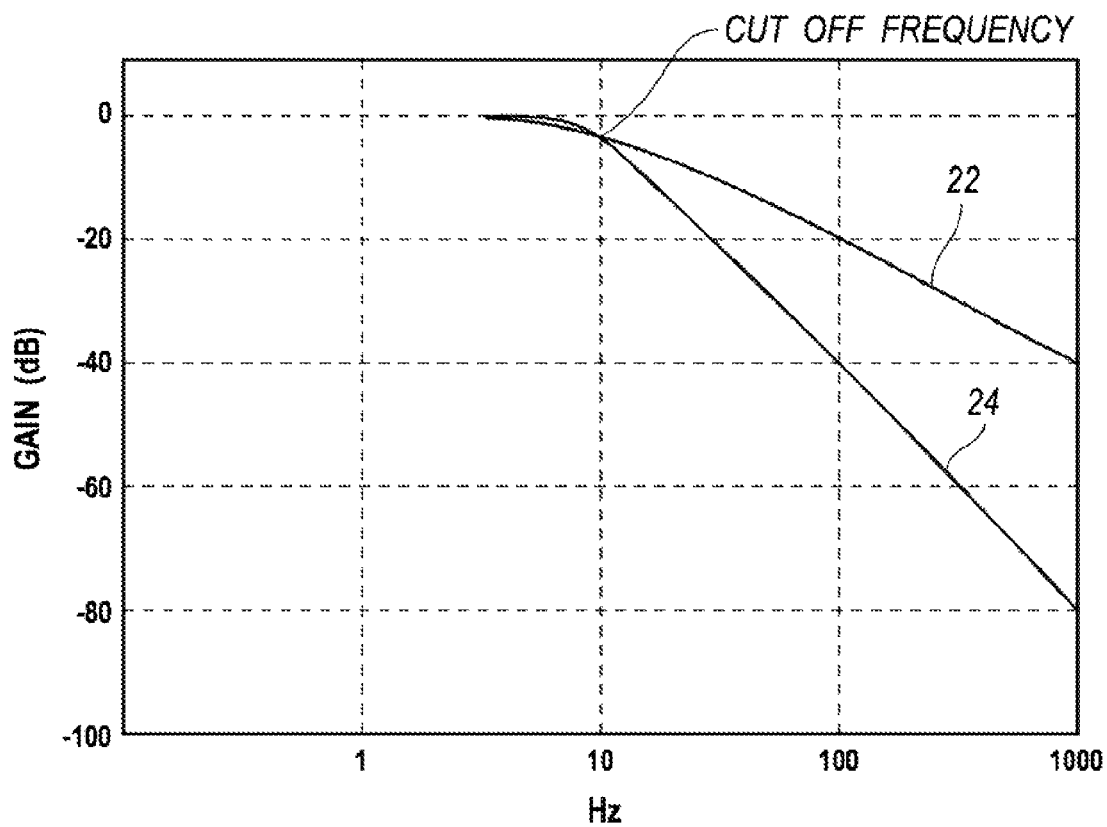
FIG. 2 is a Bode magnitude plot of the first and second fluidic devices and the combination of the first and second fluidic devices.

As shown in FIG. 2, the first fluidic device 14 and second fluidic device 16 of the preferred embodiments attenuate pulsations with a relatively shallow rolloff slope 22. For the purposes of this document, a shallow rolloff slope is defined as less than or equal to 20 dB/decade (as conventionally understood in a Bode magnitude plot of log magnitude against log frequency, and as displayed as the absolute value of the slope). The first fluidic device 14 and the second fluidic device 16 are connected to the fluidic channel 12, however, such that they preferably cooperatively attenuate pulsations with a relatively steep rolloff slope 24. For the purposes of this document, a steep rolloff slope 24 is defined as greater than 20 dB/decade (as conventionally understood in a Bode magnitude plot of log magnitude against log frequency, and as displayed as the absolute value of the slope). With a steep rolloff slope 24, such as greater than 20 dB/decade (or, more preferably, greater than or equal to 40 dB/decade), the pulsation attenuator 10 may be able to pass low-frequency fluctuations of the flow rate and filter high-frequency pulsations of the fluid within the fluidic channel 12. More significantly, the fluidic system may be able to rapidly adjust and stabilize the flow rate, while maintaining smooth flow. The rapid adjustment of the flow rate, which may have previously took several minutes in conventional fluidic systems and now could potentially take seconds, preferably minimizes the waste of the fluid within the fluidic system. The cutoff frequency is preferably less than or equal to 10 Hz and more preferably equal to 2 Hz, but may be any suitable cutoff frequency based on the needs of the fluidic system 18.

As shown in FIG. 1, the fluidic channel 12 of the preferred embodiments functions to carry fluid, such as a sample fluid, in the fluidic system 18. The fluid channel is preferably a rigid or flexible pipe, but may be any suitable fluidic device that carries fluid.

The first fluidic device 14 and the second fluidic device 16 of the preferred embodiments function to attenuate pulsations. For the purposes of this document, the term "pulsations" is defined as the periodic phenomenon that alternately increases and decreases either the pressure or flow rate of the fluid within the fluidic system. The first fluidic device 14 preferably includes a first fluidic resistor 26 and a first fluidic capacitor 28, and the second fluidic device 16 preferably includes a second fluidic resistor 30 and a second fluidic capacitor 32. For economic reasons, the first fluidic device 14 and the second fluidic device 16 are preferably substantially similar. In alternative variations, the first fluidic device 14 and the second fluidic device 16 may be different fluidic devices and/or may have different fluidic values.

Figure 3:
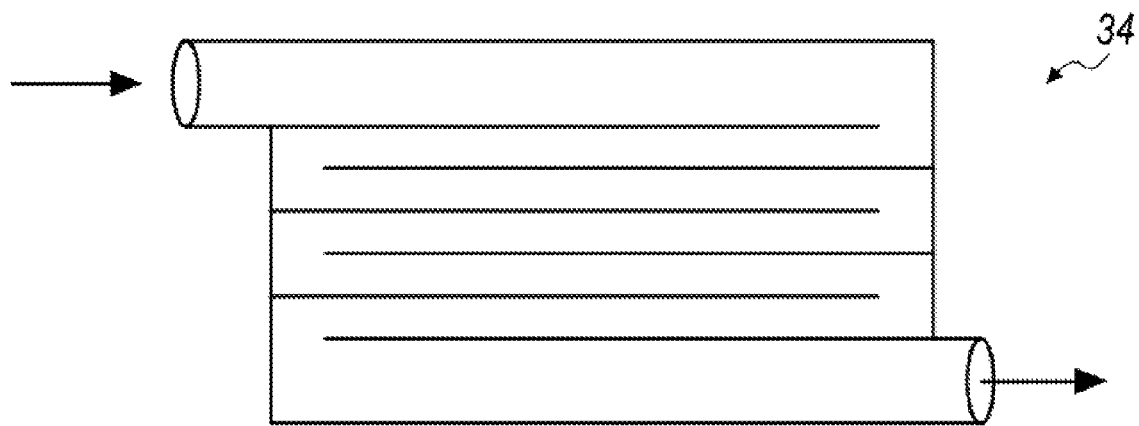
FIGS. 3 and 4 are variations of the fluidic resistors.
Figure 4:
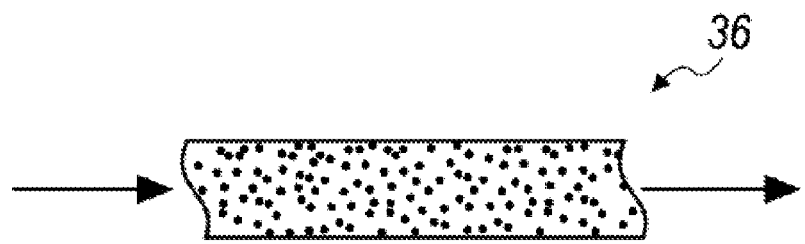

The first fluidic resistor 26 and the second fluidic resistor 30 function to resist the flow of the fluid within the fluidic channel 12. The first fluidic resistor 26 and the second fluidic resistor 30 are preferably a narrow-channel-type or a long-channel-type fluidic resistor 34 (which is shown in a space-saving serpentine-type arrangement in FIG. 3) or a ball-type fluidic resistor 36 (as shown in FIG. 4), but may be any suitable fluidic device to resist the flow of the fluid within the fluidic channel 12.

Figure 5:
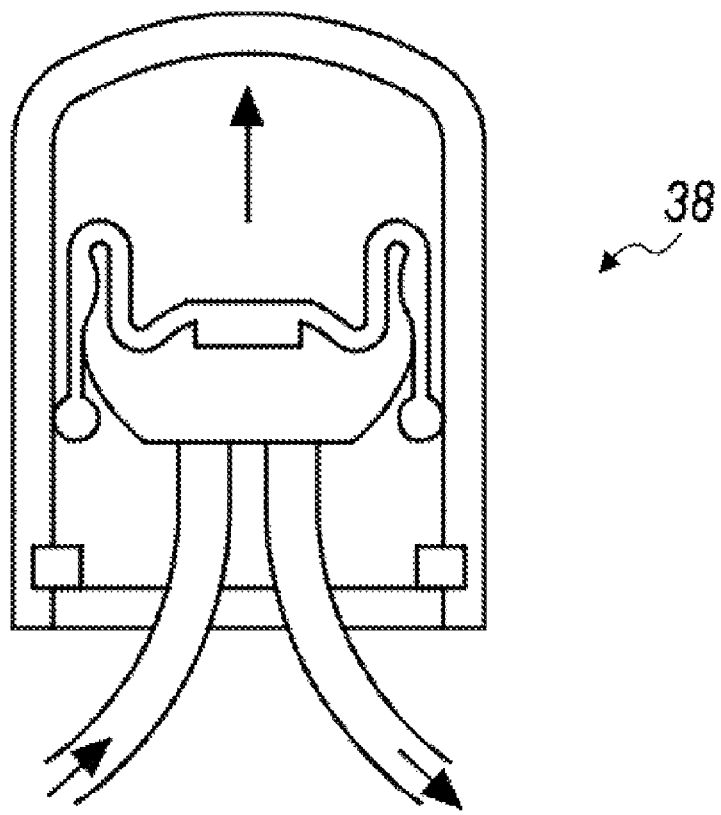
FIGS. 5 and 6 are variations of the fluidic capacitors.
Figure 6:
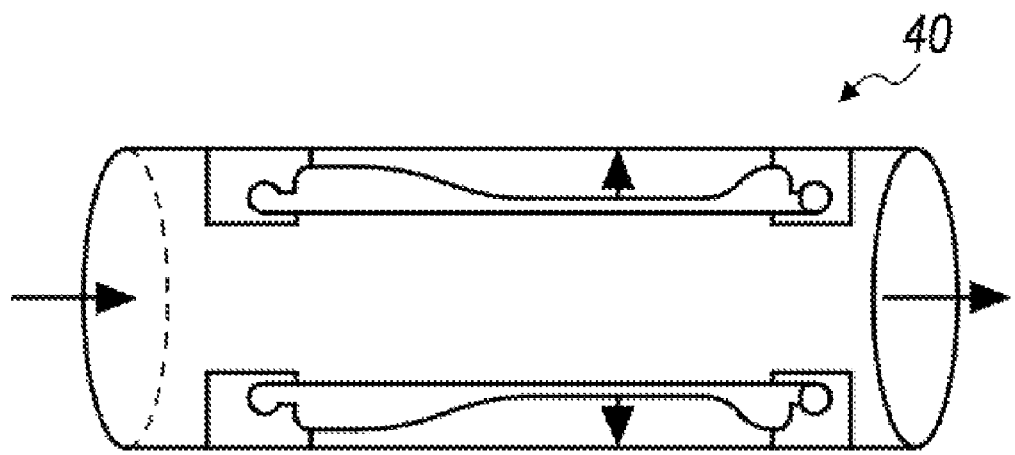

The first fluidic capacitor 28 and the second fluidic capacitor 32 function to temporarily expand and accumulate fluid (and, hence, pressure) within the fluidic channel 12 and to later contract and reintroduce the accumulated fluid (and, hence, pressure) to the fluidic channel 12. The first fluidic capacitor 28 and the second fluidic capacitor 32 are preferably a bellows-type fluidic capacitor 38 (as shown in FIG. 5) or a flexible tube-type fluidic capacitor 40 (as shown in FIG. 6), but may be any suitable fluidic device to temporarily expand and later contract. The bellows-type fluidic capacitor 38, for example, may be made without an actual diaphragm between the fluid of the fluidic channel and the compressible fluid (such as air) of the bellows-type fluidic capacitor 38. Instead of a diaphragm, the bellows-type fluidic capacitor 38 could rely on gravity or any other suitable method or device to keep the two fluids separate.

As shown in FIG. 1, the first fluidic device 14 and the second fluidic device 16 are preferably configured and arranged to attenuate pulsations above a cutoff frequency (similar to an electronic low-pass filter). More specifically, the first fluidic device 14 includes the first fluidic resistor 26 followed by the first fluidic capacitor 28, and the second fluidic device 16 includes the second fluidic resistor 30 followed by the second fluidic capacitor 32. Thus, the fluid flowing through the pulsation attenuator 10 encounters the following elements in this order: (1) the first fluidic resistor 26, (2) the first fluidic capacitor 28, (3) the second fluidic resistor 30, and (4) the second fluidic capacitor 32. In this arrangement, the pulsation attenuator 10 is similar to a second-order electronic low-pass filter with a rolloff slope of −40 dB/decade.

The pulsation attenuator 10 may, alternatively, include more than two fluidic devices. In a pulsation attenuator 10 that includes five fluidic devices, for example, the fluid encounters the following elements in this order: (1) the first fluidic resistor 26, (2) the first fluidic capacitor 28, (3) the second fluidic resistor 30, (4) the second fluidic capacitor 32, (5) a third fluidic resistor, (6) a third fluidic capacitor, (7) a fourth fluidic resistor, (8) a fourth fluidic capacitor, (9) a fifth fluidic resistor, and (10) a fifth fluidic capacitor. In this arrangement, the pulsation attenuator 10 is similar to a fifth-order electronic low-pass filter with a rolloff of −100 dB/decade. The first fluidic device 14 and the second fluidic device 16 may be alternatively configured and arranged to attenuate pulsations below a cutoff frequency (similar to an electronic high-pass filter). Further, the pulsation attenuator 10 of alternative embodiments may be arranged in any suitable order and may have any suitable number of fluidic devices, fluidic resistors, and fluidic capacitors, including a combination of a "low-pass" pulsation attenuator and a "high-pass" pulsation attenuator that would either attenuate pulsations within two frequencies (similar to an electronic band-stop filter) or outside of two frequencies (similar to an electronic band-pass filter).

2. The Pulsation Attenuator of the Second Preferred Embodiment

Figure 7:
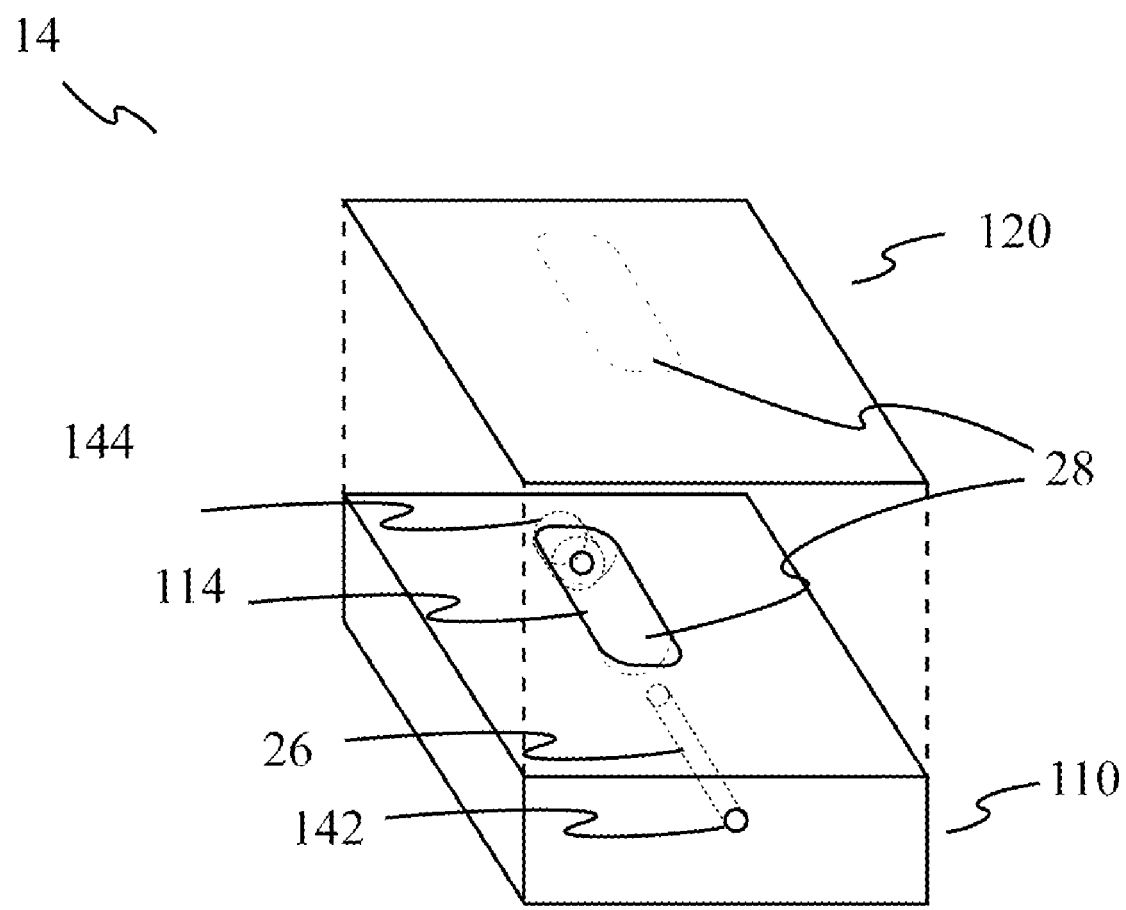
FIGS. 7 and 8 are exploded schematic representations of a pulsation attenuator of a second preferred embodiment.
Figure 8:
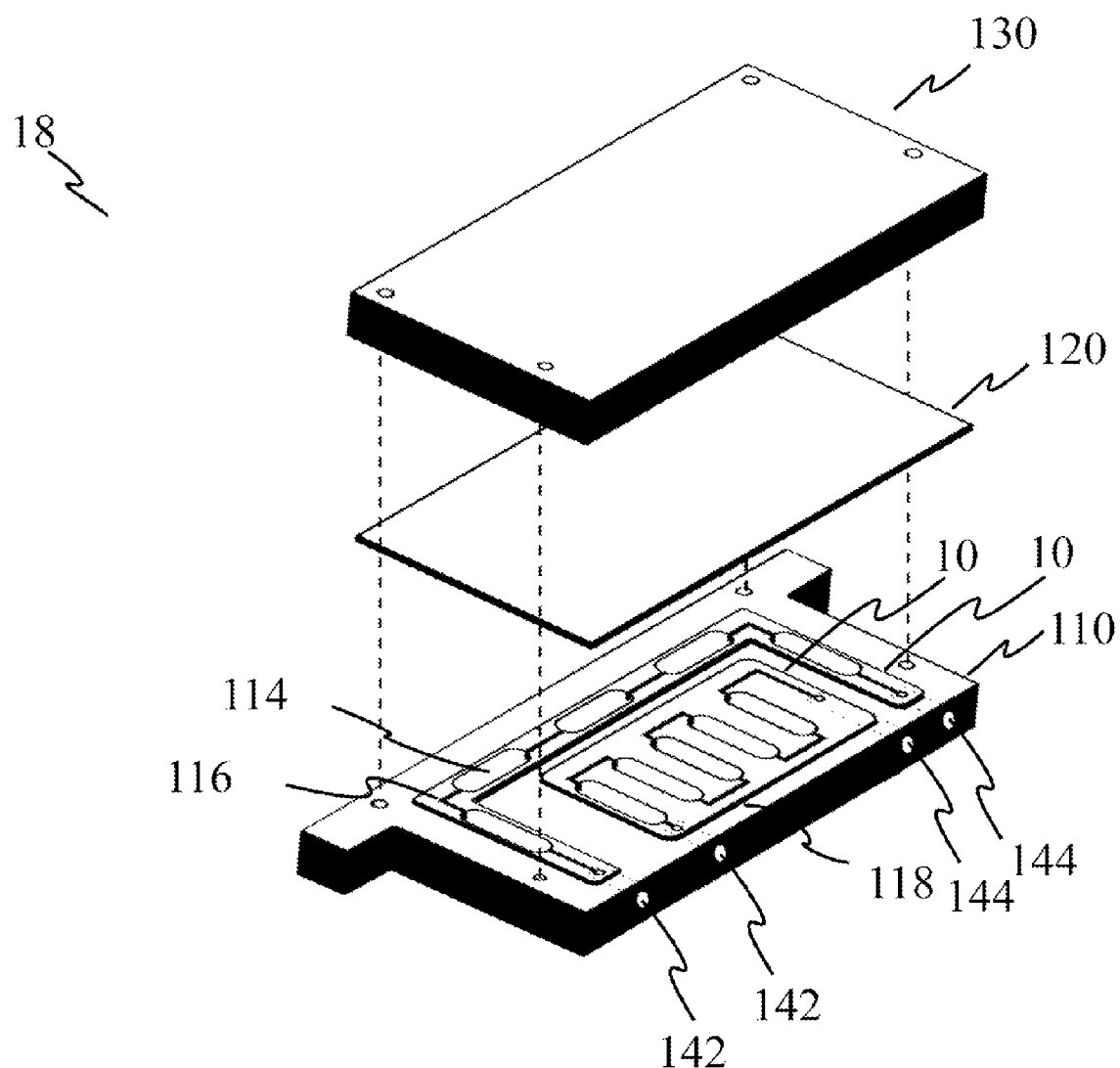

As shown in FIG. 7, the second preferred embodiment of a fluidic device includes a bottom plate 110 and a membrane sheet 120. The bottom plate 110 and membrane sheet 120 preferably cooperate to form the structure of a fluidic capacitor and/or a fluidic resistor. As shown in FIG. 8, a top plate 130 may additionally be used to facilitate fluidically sealing and/or forming the fluidic device. The bottom plate 110, the membrane sheet 120, and additionally the top plate 130 are preferably used to form the fluidic device of the first fluidic device 14, the second fluidic device 16, and/or any fluidic device of the pulsation attenuator 10 as described above. A fluidic channel preferably connects to the preferred embodiment of the fluidic device or alternatively multiple fluidic channels connect to the fluidic device. The fluidic device(s) additionally has an inlet 142 and outlet 144 for fluid to flow into and out of the fluidic device. The inlet 142 and outlet 144 are preferably in fluidic contact with the fluidic device(s). A fluidic device of the pulsation attenuator 10 may alternatively be designed in any suitable means.

Figure 9:
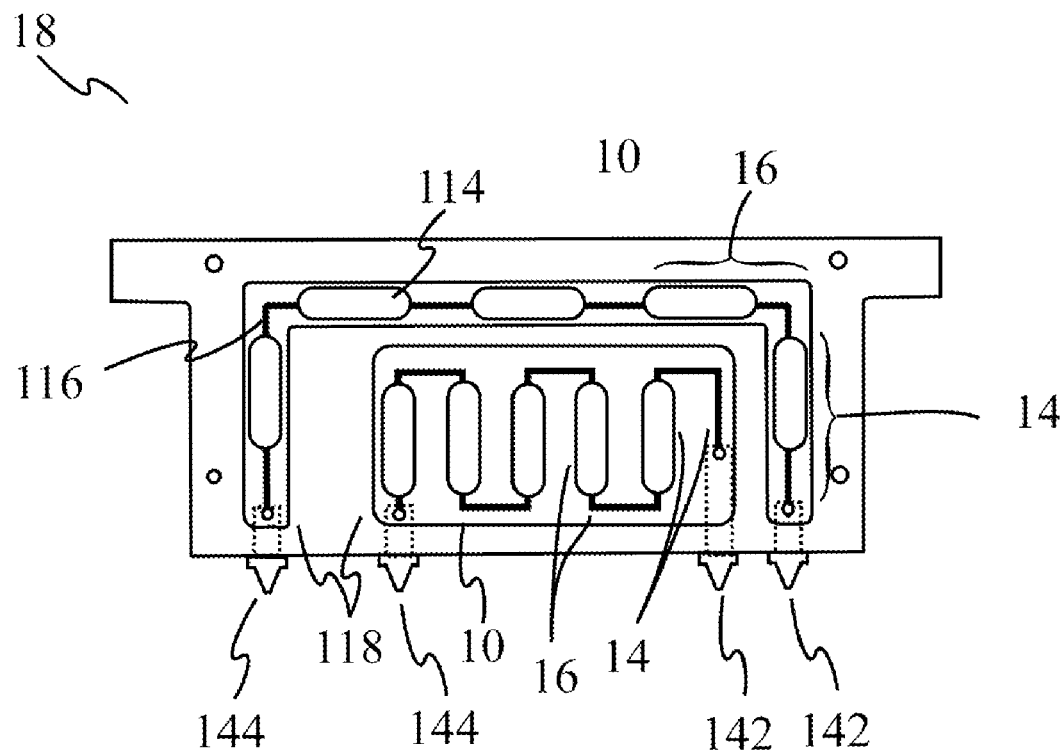
FIGS. 9 and 10 are detailed views of the bottom plate and the top plate, respectively, of the pulsation attenuator of the second preferred embodiment.

As shown in FIGS. 7-9, the bottom plate 110 functions to form part of a fluidic device. More preferably, the bottom plate 110 functions as a component of a fluidic resistor and/or a fluidic capacitor. The bottom plate 110 is preferably a machined metal plate, but the bottom plate 110 may alternatively be any suitable geometry, material, or manufactured in any suitable way, such as an injection or blow molded plastic part, 3D printed part, or a cast part. The bottom plate 110 preferably cooperates with the membrane sheet 120 to form a fluidic capacitor. The bottom plate 110 preferably has a bottom open well 114 that is an opening defined or formed along a first surface of the bottom plate 110. The bottom open well 114 preferably has an opened side that interfaces with the membrane sheet 120 to seal the fluidic capacitor. An amount of fluid preferably fills a volume defined by the open well 114 and the membrane sheet 120. The volume is preferably variable with the expansion and contraction of the membrane sheet 120. The bottom plate 110 may additionally or alternatively form the fluidic resistor of the fluidic device. The fluidic resistor is preferably a narrow channel that is fully or partially defined by the bottom plate 110. The fluidic resistor may alternatively be a long channel, a ball-type fluidic resistor, or any suitable resistive channel. The narrow channel is preferably narrower than the fluidic channel. In one variation, the narrow channel is a blind hole (not milled or drilled fully through the bottom plate 110), preferably in the side of the bottom plate 110. The blind hole preferably starts at an inlet 142 or outlet 144 and leads to a fluidic resistor or an open well 114 of a fluidic capacitor. In a second variation, the narrow channel is an open channel 116 that partially forms an enclosed channel and is located along a surface of the bottom plate 110. The open well 114 and the open channel are preferably on the side surface of the bottom plate 110. In this variation, the membrane sheet 120, a top plate, and/or any suitable device cooperate to fully enclose and seal the fluidic resistor. Additionally, the open well 114 and the open channel 116 are preferably made by milling or made with a computer numerical control (CNC) device on a single side of a metal plate.

As shown in FIGS. 7 and 8, the membrane sheet 120 functions as a bellow or diaphragm of a fluidic capacitor. The membrane may additionally or alternatively function as a gasket to seal open portions of the bottom plate. The membrane sheet 120 is preferably a non-permeable elastic sheet such as silicone or latex. The membrane sheet 120 may alternatively be any suitable material that preferably facilitates expansion and contraction. The expansion and contraction of the membrane sheet 120 (e.g. the elasticity) preferably provides a restoring force that contributes to the capacitive nature of a fluidic capacitor. The membrane sheet 120 may alternatively not provide a substantial restoring force, and the restoring force may be provided by other suitable means such as by air pressure. The membrane sheet 120 is preferably fixed onto the bottom plate 110, or more preferably, pressed or held in between the bottom plate 110 and a top plate 130. The membrane sheet 120 may alternatively be insert molded, adhered, or attached to the bottom plate in any suitable manner. The membrane sheet may alternatively be a non-planar sheet or form. In one variation, the membrane sheet 120 is a flexible structure that is insert molded onto the bottom plate, substantially sealing the fluidic device and forming a flexible bellow for the fluidic capacitor.

Figure 10:
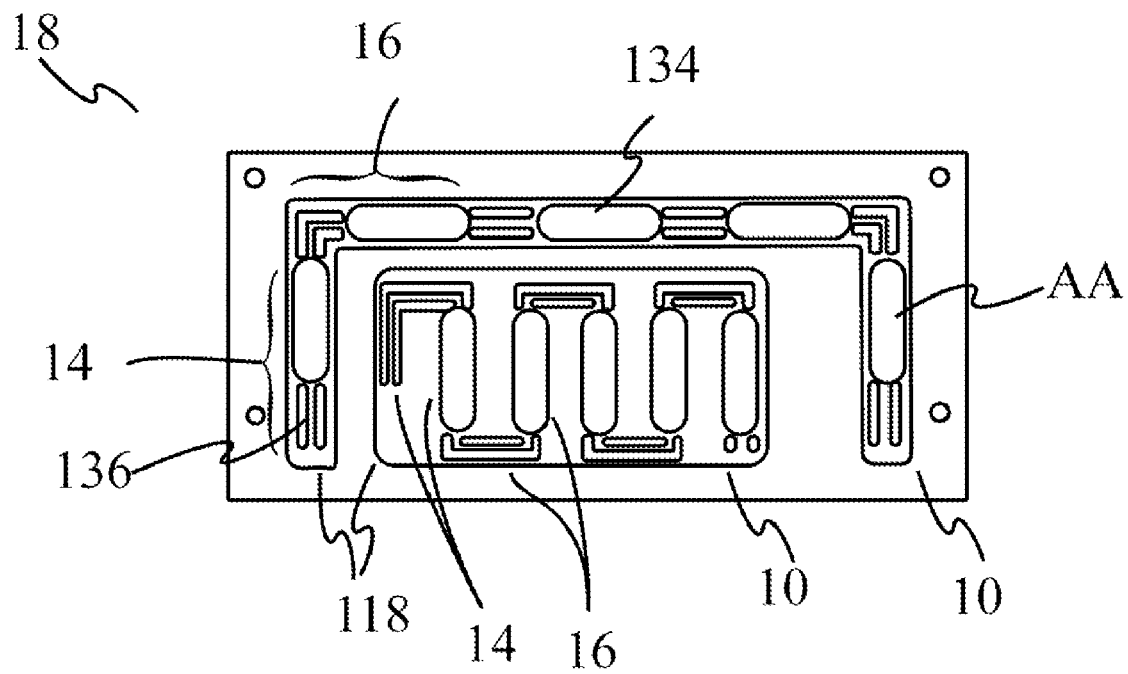

As shown in FIGS. 8 and 10, the additional alternative of a top plate 130 functions to secure the membrane sheet 120 to the bottom plate 110. The top plate 130 is preferably made from substantially similar material and/or manufacturing processes as the bottom plate 110, but the bottom plate 110 and top plate 130 may alternatively have different materials, form, or manufacturing processes. The top plate 130 preferably has at least one surface that is formed to align and interface with the surface of the bottom plate 110. Preferably this surface is a flat surface to interface with the flat surface of the bottom plate 110. The bottom plate 110 and top plate 130 may additionally have corresponding insets 118 that align the components of the fluidic devices. Alternatively, the top plate 130 may have any suitable shape that facilitates being attached to the bottom plate 110. The top plate 130 preferably has a top open well 134 substantially similar to the bottom open well 114 of the bottom plate 110 except as described. The top open well 134 preferably functions to define a volume that fluid may fill. The membrane sheet 120 preferably prevents the fluid from making contact with the top plate 130, but the top open well 134 may alternatively contact the fluid. The membrane sheet 120 and the top open well 134 preferably form a sealed air chamber. The sealed air chamber preferably becomes pressurized, exerting a force on the membrane sheet 120, based on the volume of the top plate well 134 occupied by a fluid. The pressure provides a restoring force that contributes to the capacitive nature of a fluidic capacitor. The restoring force generated by a sealed air chamber may be used additionally or alternatively to a restoring force provided by the membrane sheet 120. The top plate 130 may additionally include channel seal structure 136 that is shaped to align and seal open surfaces of the bottom plate 110. The channel seal structure 136 preferably seals the open channel of the resistive channel 112. The channel seal structure 136 is preferably a rib or inset that substantially covers open surfaces such as the open channel 116. Additionally the channel seal structure 136 may cooperate with the membrane sheet 120 to improve the sealing of the fluidic device (such as by tightening the membrane sheet).

The bottom plate 110 and the top plate 130 of the preferred embodiment are preferably bolted together. The bottom plate 110 and the top plate 130 preferably have corresponding screw holes that enable bolts to fasten the bottom plate 110 and the top plate 130 together. The bottom plate 110 and the top plate 130 may alternatively be attached by a press-fit, a latch, spring pressed, clamped, adhered, and/or any suitable means to attach the bottom plate 110 and the top plate 130.

As an alternative, the bottom plate 110 and membrane sheet 120 may be adapted to form any number of fluidic devices for any number of fluidic channels. The bottom plate 110 and membrane sheet 120 may be designed to form any number of fluidic resistors and/or any number of fluidic capacitors. Additionally, the top plate 130 may additionally be used with the bottom plate 110 and membrane sheet 130 to form any suitable number of fluidic devices, fluidic resistors and/or fluidic capacitors. As shown in FIGS. 8-10, in one variation, the bottom plate 110, the membrane sheet 120, and the top plate 130 cooperate to form five fluidic devices for a first fluidic channel and five fluidic devices for a second fluidic channel. The fluidic devices preferably each have a fluidic resistor and fluidic capacitor as described above. The fluidic devices are preferably in series but alternatively may be arranged in any suitable configuration such as in parallel, series, or a combination of parallel and series with varying fluidic resistances or capacitance. In an application in the flow cytometer field, the first fluidic channel and the second fluidic channel are preferably connected to one of the following: a sheath fluid channel or a waste fluid channel (sheath fluid plus sample fluid). The fluidic devices of the two fluidic channels may be arranged in any suitable pattern such as a straight or serpentine (winding back and forth). In one variation, the fluidic devices of a first fluidic channel perform a serpentine pattern and the fluidic devices of a second fluidic channel are positioned along the outside of the serpentine pattern as shown in FIGS. 8-10.

As a person skilled in the art of fluidic systems for flow cytometers will recognize from the previous detailed description and from the figures and claims, modifications and changes can be made to the preferred embodiment of the invention without departing from the scope of this invention defined in the following claims.

We claim:

1. A pulsation attenuator for a fluidic system with a fluidic pump, comprising:
   a fluidic channel;
   a first fluidic device connected to the fluidic channel and adapted to attenuate pulsations, wherein the first fluidic device includes a first fluidic resistor and a first fluidic capacitor;
   a second fluidic device connected to the fluidic channel and adapted to attenuate pulsations, wherein the second fluidic device includes a second fluidic resistor and a second fluidic capacitor;
   wherein the first fluidic resistor and the second fluidic resistor are resistive channels; and
   wherein the first fluidic capacitor and the second fluidic capacitor include a membrane that expands and accumulates fluid and then contracts and reintroduces the accumulated fluid into the fluidic channel.

2. The system of claim 1, wherein the system includes a bottom plate, wherein the membrane is a membrane sheet secured to the bottom plate, wherein the bottom plate and membrane sheet cooperate to form the first fluidic capacitor.

3. The system of claim 2, wherein the membrane sheet provides a restoring force of the first fluidic capacitor.

4. The system of claim 2, wherein the bottom plate includes the resistive channel of the first fluidic resistor.

5. The system of claim 4, wherein the resistive channel is a narrow channel.

6. The system of claim 4, wherein the first fluidic device further includes a top plate that interfaces with the bottom plate and that secured the membrane sheet between the bottom plate and the top plate, and wherein the bottom plate, the top plate, and the membrane sheet cooperate to form the first fluidic capacitor.

7. The system of claim 6, wherein the membrane sheet fluidically seals the interface of the bottom plate and top plate.

8. The system of claim 7, wherein the second fluidic device is substantially similar to the first fluidic device.

9. The system of claim 8, wherein the bottom plate, the top plate, and the membrane sheet form the first fluidic device and the second fluidic device.

10. The system of claim 9, wherein the first fluidic resistor and the second fluidic resistor have different fluidic resistance and the first fluidic capacitor and the second fluidic capacitor have different fluidic capacitance.

11. The system of claim 9, wherein the bottom plate, the top plate, and the membrane sheet additionally cooperate to form a second fluidic channel with an associated third fluidic device and fourth fluidic device, wherein the first, second, third, and fourth fluidic devices are substantially similar.

12. The system of claim 7, wherein the bottom plate includes a bottom open well that is defined along a first surface of the bottom plate, wherein the bottom open well forms a portion of the first fluidic capacitor; wherein the top plate includes a top open well that is define along a first surface of the top plate, wherein the top open well forms a portion of the first fluidic capacitor; and wherein the bottom open well aligns with the top open well.

13. The system of claim 12, wherein the top open well and membrane sheet form a sealed air chamber that can generate a restoring force of the first fluidic capacitor.

14. The system of claim 12, wherein the bottom plate includes:

an inlet that communicates with the first fluidic resistor and first fluidic capacitor;

an outlet that communicates with the inlet via the first fluidic resistor and first fluidic capacitor.

15. The system of claim 14, wherein the resistive channel is an open channel defined along the first surface of the bottom plate; and wherein the top plate includes a channel seal structure that is shaped to mate and seal the surface of the bottom plate along the resistive channel.

16. The system of claim 15, wherein the bottom plate and the top plate have corresponding insets that align the first surface of the bottom plate and the first surface of the top plate.

17. The system of claim 16, wherein the top plate and bottom plate are fastened together causing the corresponding insets to tighten the membrane sheet around the first fluidic resistor and first fluidic capacitor.

18. The system of claim 15, wherein the second fluidic device is substantially similar to the first fluidic device.

19. The system of claim 18, wherein the bottom plate, the top plate, and the membrane sheet form the first fluidic device and the second fluidic device.

20. The system of claim 19, wherein the bottom plate, the top plate, and the membrane sheet form five connected fluidic devices for a first fluidic channel, each fluidic device having a fluidic resistor and fluidic capacitor.

21. The system of claim 20, wherein the bottom plate, the top plate, and the membrane sheet further form a five connected fluidic devices for a second fluidic channel, each fluidic device having a fluidic resistor and fluidic capacitor.

22. The system of claim 21, wherein the five connected fluidic devices for the first fluidic channel are arranged in a substantially serpentine pattern and the five connected fluidic devices for the second fluidic channel are arranged outside of perimeter of the serpentine arrangement.

* * * * *

UNITED STATES PATENT AND TRADEMARK OFFICE
CERTIFICATE OF CORRECTION

| | | |
|---|---|---|
| PATENT NO. | : 7,857,005 B2 | |
| APPLICATION NO. | : 12/425830 | |
| DATED | : December 28, 2010 | |
| INVENTOR(S) | : Collin A. Rich and Nathaniel C. Bair | |

It is certified that error appears in the above-identified patent and that said Letters Patent is hereby corrected as shown below:

In column 6, line 40, "secured" should read --secures--
In column 6, line 64, "define" should read --defined--
In column 8, line 13, "form a five" should read --form five--
In column 8, lines 19-20, "outside of perimeter" should read --outside of the perimeter--

Signed and Sealed this
Twenty-second Day of February, 2011

David J. Kappos
*Director of the United States Patent and Trademark Office*